United States Patent
Van Esch et al.

(10) Patent No.: US 10,245,316 B2
(45) Date of Patent: Apr. 2, 2019

(54) HYPO-ALLERGENIC CROSS-LINKED PROTEINS FOR USE IN THE PREVENTION OF AN ALLERGY AGAINST MILK-PROTEINS AND FOR USE IN THE INDUCTION OF ORAL TOLERANCE

(71) Applicant: Friesland Brands B.V., Amersfoort (NL)

(72) Inventors: Elisabeth Catharina Adriana Maria Van Esch, Utrecht (NL); Marjan Gros-Van Hest, Renkum (NL); Erik Labij, Ede (NL); Johannes Martinus Maria Westerbeek, Woerden (NL)

(73) Assignee: FRIESLAND BRANDS B.V., Amersfoort (NL)

( * ) Notice: Subject to any disclaimer, the term of this patent is extended or adjusted under 35 U.S.C. 154(b) by 1003 days.

(21) Appl. No.: 14/414,387

(22) PCT Filed: Jul. 12, 2013

(86) PCT No.: PCT/NL2013/050533
§ 371 (c)(1),
(2) Date: Jan. 12, 2015

(87) PCT Pub. No.: WO2014/011052
PCT Pub. Date: Jan. 16, 2014

(65) Prior Publication Data
US 2015/0196633 A1 Jul. 16, 2015

(30) Foreign Application Priority Data

Jul. 13, 2012 (EP) .................................... 12176365

(51) Int. Cl.
| | | |
|---|---|---|
| *A61K 39/35* | (2006.01) | |
| *A61K 38/17* | (2006.01) | |
| *A23L 33/00* | (2016.01) | |
| *A23L 33/19* | (2016.01) | |
| *C07K 14/47* | (2006.01) | |

(52) U.S. Cl.
CPC .............. *A61K 39/35* (2013.01); *A23L 33/19* (2016.08); *A23L 33/40* (2016.08); *A61K 38/1709* (2013.01); *C07K 14/4732* (2013.01)

(58) Field of Classification Search
None
See application file for complete search history.

(56) References Cited

U.S. PATENT DOCUMENTS 6,190,724 B1 * 2/2001 Sawatzki ............... A23C 11/04
426/580
2004/0265463 A1 * 12/2004 Hendrickx ........... A23C 19/082
426/582

FOREIGN PATENT DOCUMENTS

JP 03-027253 A 2/1991
WO WO-01/70042 A1 9/2001

OTHER PUBLICATIONS

Juvonen et al.Crosslinking with transglutaminase does not change metabolic effects of sodium caseinate in model beverage in healthy young individuals.' Nutr. J. 11:35, 2012. pp. 1-12.*
Juvonen et al. 'Structure modification of a milk protein-based model food affects postprandial intestinal peptide release and fullness in healthy young men.' Br. J. of Nutr. 106:1890-1898, 2011.*
Hochwaller et al. Cow's milk allergy: From allergens to new forms fo diagnosis, therapy and prevention.' Methods 66:22-33, 2014.'.*
Fritsché et al., "Induction of systemic immunologic tolerance to BETA-lactoglobulin by oral administration of a whey protein hydrolysate", J. Allergy Clin. Immunol, Aug. 1997, vol. 100, No. 2, pp. 266-273.
Guo et al., "Susceptibility of 3B2-lactoglobulin and sodium caseinate to proteolysis by pepsin and trypsin., Journal of Dairy Science," 1995, vol. 78, No. 11, pp. 2336-2344.
Van Esch et al., "Oral tolerance induction by partially hydrolyzed whey protein in mice is associated with enhanced numbers of Foxp3+ regulatory T-cells in the mesenteric lymph nodes," Pediatric Allergy Immunology, 2011, vol. 22, pp. 820-826.
Clare D.A. et al., "Transglutaminase polymerization of peanut proteins", Journal of Agricultural and Food Chemistry, vol. 55, No. 2, Jan. 2007, pp. 432-438.
International Search Report of PCT/NL2013/050533 dated Oct. 21, 2013.
Stanic, D. et al., "Digestibility and allergenicity assessment of enzymatically crosslinked beta-casein", Molecular Nutrition & Food Research, vol. 54, No. 9, Sep. 2010, pp. 1273-1284.
Van Esch, B.C.A.M. et al., "Sensitizing capacity and allergenicity of enzymatically cross-linked sodium caseinate in comparison to sodium caseinate in a mouse model for cow's milk allergy", Toxicology Letters (Shannon), vol. 218, No. 1, Jan. 23, 2013, pp. 50-55.
Villas-Boas, M.B. et al., "The effect of transgluatminase-induced polymerization in the presence of cystein on beta-lactoglobulin antigenicity", International Dairy Journal, vol. 20, No. 6, Jun. 2010, pp. 386-392.
Wal, J.M., "Cow's milk allergens," Allergy, 1998, vol. 53, 1013-1022.
Kaminogawa et al., "Molecular biology of the oral immunization generosity", The Molecular Biology of Oral Tolerance—Protein, Nucleic Acid and Enzyme, 1994, vol. 39, No. 12, 44 pages, with English language machine translation.

* cited by examiner

*Primary Examiner* — G. R. Ewoldt
(74) *Attorney, Agent, or Firm* — Gilberto M. Villacorta; Sunit Talapatra; Foley & Lardner LLP

(57) ABSTRACT

The present invention provides a hypo-allergenic cross-linked protein for use in the prevention of an allergy against milk proteins, or for use in the induction of oral tolerance for milk proteins, said cross-linked protein being selected from cross-linked casein, cross-linked caseinate and combinations thereof. The invention further provides a nutritional composition for use in the prevention of an allergy against milk proteins or for use in the induction of oral tolerance against milk proteins.

20 Claims, No Drawings

HYPO-ALLERGENIC CROSS-LINKED PROTEINS FOR USE IN THE PREVENTION OF AN ALLERGY AGAINST MILK-PROTEINS AND FOR USE IN THE INDUCTION OF ORAL TOLERANCE

FIELD OF THE INVENTION

The present invention relates to hypo-allergenic cross-linked proteins for use in the prevention of an allergy against milk proteins, such as cow's milk proteins, or for use in the induction of oral tolerance against such proteins. The invention relates further to a nutritional composition comprising said hypo-allergenic cross-linked proteins for use in the prevention of an allergy against milk proteins, or for use in the induction of oral tolerance against milk proteins, and to a hypo-allergenic nutritional composition.

BACKGROUND OF THE INVENTION

Food allergies, of which the first to occur in life is most often cow's milk allergy, are caused, in most cases, by a reaction to proteins in food. Various cow's milk proteins, e.g. β-lactoglobulin, casein, α-lactalbumin and serum albumin have been identified as allergens (Wal, J. M. (1998) Cow's milk allergens, *Allergy*, 53, 1013-1022). Also proteins derived from cow's milk, such as caseinate have been identified as allergens.

In the early years of life the human immune system is still developing and may fail to develop (oral) tolerance to dietary antigens. The result is that a human subject, such as a baby or child mounts an exaggerated immune response to the dietary protein and develops an allergic response to it.

Most often, food hypersensitivity develops just after a susceptible baby or child first encounters a new food containing potential allergens. Apart from its mother's milk, the first dietary proteins generally encountered by human babies are cow's milk proteins and, as noted above, cow's milk allergy is the most common food allergy in human babies. It is generally accepted that babies with established cow's milk allergy also have an increased risk of developing allergies to other dietary proteins such as egg and cereal proteins. All these allergies may manifest themselves clinically as atopic diseases such as atopic dermatitis, intestinal problems, eczema and asthma. Hence, a need exists to prevent or treat such allergies.

Without the intention to be bound by any theory it is believed that, food derived proteins are in persons susceptible to food allergy responsible for the induction of type 1(acute)-hypersensitivity reactions after initial sensitization. Type 1 allergic reactions to food proteins leading to food allergy are characterized in majority by T helper 2 (Th2) polarization of the immune response resulting in the production of allergen-specific IgE (sensitization phase).

Binding of IgE to the high affinity receptor FcεR1 on mast cells and basophils followed by subsequent cross-linking of the receptors by the specific allergen provokes degranulation (effector/challenge phase). The release of mediators such as histamine, leukotriens and cytokines results in clinical symptoms involving the skin, gastrointestinal tract, airways and sometimes anaphylaxis within a few minutes to one hour after ingestion of the specific food.

From a dietary point of view a need thus exists to prevent the development of an allergy against milk proteins, such as cow's milk proteins. This is of importance because very often cow's milk or milk from other mammals is used to supplement or completely replace human breast milk fed to babies.

In general, postponing the contact with intact milk protein prevent subjects from developing an allergy against milk proteins, such as cow's milk proteins. Basically, there are two ways to postpone the contact with intact milk protein.

The first way is to completely avoid foods containing milk proteins. However, such diets have the disadvantage that compliance is low because available foodstuffs are very restricted. Moreover, for infants, cow's milk protein-based formula have been determined as the best alternative for human breastmilk.

A second way to prevent the development of an allergy against milk proteins is to alter the allergenic properties of the milk proteins by hiding, destroying or disclosing allergic epitopes through conformational changes in proteins, or by improving the access of the hidden epitopes located within the protein to the gastrointestinal enzymes (Guo et al., (1995), Susceptibility of ε-lactoglobulin and sodium caseinate to proteolysis by pepsin and trypsin., *Journal of Dairy Science*, 78, 2336-244).

One commonly applied method is to extensively hydrolyse the (potential) allergenic food proteins. However, most often these kinds of products have a poor taste and poor functional properties, such as insolubility, impaired emulsification capacity, and/or poor rheological properties. Moreover, by extensive hydrolysis, these proteins may lose their capability to induce oral tolerance. This means that the subject will still be sensitive to develop an allergy when it ingests the intact protein.

Another way of preventing a food allergy is to induce oral tolerance by way of administering over a period of several weeks relatively small amounts of the allergenic protein, such as cow's milk proteins, to human subjects. It may also be possible to administer the allergenic protein to subjects at risk of developing allergy in (slightly) changed form. For this purpose (partially) hydrolyzed proteins are used.

In Fritsché et al. (J. Allergy Clin. Immunol, Vol 100, No. 2, pages 266-273, 1997) it is shown in animal models that the usage of enzymatically hydrolysed milk proteins with a degree of hydrolysis of 18% were able to induce oral tolerance to intact cow's milk proteins. Results of these experiments showed that feeding of rats with such hydrolysed cow's milk proteins, whose allergenicity had been reduced over 100 times as compared to untreated proteins, suppressed the allergic reaction.

Also in van Esch et al. (Pedriatic allergy and immunology, 2011:22:820-826) it has been shown that whey protein hydrolysates have the capacity to induce oral tolerance to whey.

However, as already indicated above, the enzymatic hydrolysis of food proteins, in particularly cow's milk proteins, causes a poor taste and poor functional and/or rheological properties, which is particularly the case with food products wherein the casein is hydrolyzed. Such a poor taste and lack of good functional and/or rheological properties has to be masked with other ingredients, which further increases the costs and complexity of the process and the product.

Another way of lowering the antigenicity of food proteins is to polymerize or cross-link these proteins (Clare, D. A. et al., 2007, Transglutaminase polymerization of peanut proteins. *Journal of Agriculture and Food Chemistry*, 55, 432-438.).

In a study of Villas-Boas et al. the effect of transglutaminase induced polymerization on the antigenicity of β-lactoglobulin has been examined (Villas-Boas, M. B., et al. 2010, The effect of transglutaminase-induced polymerization in the presence of cysteine on β-lactoglobulin antigenicity, *International Dairy Journal,* 20, 6, pp 386-392.). In this study additional agents, such as cysteine, had to be used in order to be able to treat the β-lactoglobulin with transglutaminase. Moreover, it was shown that the pepsin digestion carried out of the polymerized samples did not suppress the antigenicity of β-lactoglobulin.

In the article of Stanic et al., in Mol. Nutr. Food Res. 2010., the cross-linking of casein by means of an enzymatic treatment has been described. However, in this article only subjects have been examined which had already developed an allergy against casein. Stanic et al., is silent about the non-sensitizing ability of the cross-linked caseins and does not describe the prevention of the development of an allergy against casein, nor does it describe to potential of the cross-linked casein or caseinate to induce oral tolerance.

An important milk protein present in milk is casein. Casein constitutes about 80% of the proteins in cow's milk and between 20 and 45% in human milk.

In view of the relatively high content of casein in milk (e.g cow's milk) or milk products, an allergy against this protein, its salts (caseinates) or derivates may cause considerable problems. Hence, a serious need exists to prevent allergies against these proteins, and to induce oral tolerance against them.

SUMMARY OF THE INVENTION

Surprisingly, the inventors have found a way to prevent an allergy against milk proteins, and to induce oral tolerance for them, in particularly for casein or caseinate.

The inventors have found that cross-linked casein or cross-linked caseinate administered to mammals, including human subjects, such as infants, predisposed to develop a milk protein allergy strongly reduced sensitization to develop an allergy against milk proteins, in particular cow's milk proteins, such as casein or caseinate. Hence, the development of an allergy against milk proteins, such as casein or caseinate is prevented.

It has further been found that cross-linked casein or cross-linked caseinate induced oral tolerance to the intact protein, i.e. casein or caseinate. Hence, a way is provided to prevent by means of hyposensitization therapy an allergy against milk proteins, such as casein or caseinates.

Particularly good results in the prevention of an allergy against milk proteins have been obtained when casein or caseinate is used that has been cross-linked by means of an enzymatic treatment, such as a treatment with transglutaminase.

Hence, the cross-linked casein or cross-linked caseinate according to the invention may be used for the prevention of an allergy, i.e. prevention of sensitization (e.g. measured as reduced clinical related symptoms), against milk proteins, such as casein or caseinate, in predisposed persons, such as young children, e.g. children up to 12 months, preferably up to 6 months. Moreover, it may be used to induce oral tolerance against milk proteins, such as casein and caseinate in such persons.

DEFINITIONS

The term 'hypo-allergenic' as used herein has its normal scientific meaning and refers to a situation wherein no or only a minor allergic reaction is triggered.

The term 'protein' as used herein refers to a linear polypeptide comprising at least 10 amino acid residues.

The term 'milk protein' as used herein refers to proteins present in milk from non-human mammals, such as bovines (e.g. cows), goats, sheeps or camels or to salts of such proteins (e.g. caseinate).

The term 'cow's milk' or 'cow's milk protein' refers to milk or milk proteins, respectively, derived from bovine, including cows.

The term 'allergy' as used herein has its normal scientific meaning and refers to a hypersensitivity disorder of the immune system.

The term 'casein' as used herein has its normal scientific meaning and refers to α-casein, β-casein, K-casein or the combination thereof as present in milk of mammals.

The term 'caseinate' as used herein has its normal scientific meaning and refers to salts prepared from casein present in milk.

The term 'sensitization' as used herein has its normal scientific meaning and refers to the process by which the immune system becomes more likely to respond to an allergen, by repeatedly exposing a host to a potential allergen.

The term 'allergen' as used herein has its normal scientific meaning and refers to a substance that can cause an allergic reaction.

The term 'allergenicity' as used herein has its normal scientific meaning and refers to the potential of an allergen to cause an allergic reaction.

The term 'oral tolerance' as used herein has its normal scientific meaning and refers to the active process in which the immune system of a mammal, such as a human, is stimulated in developing a normal response to an allergen by prior administration of the allergen or derivate thereof via the oral route, also referred to as 'oral immune tolerance'.

DETAILED DESCRIPTION OF THE INVENTION

A first aspect of the present invention relates to a cross-linked protein for use in the prevention of an allergy against milk proteins, or for use in the induction of oral tolerance against milk proteins, such as cow's milk proteins, wherein the cross-linked protein is selected from cross-linked casein, cross-linked caseinate or combinations thereof.

The cross-linked casein or cross-linked caseinate is preferably derived from the same kind of animal as the milk proteins for which the allergy is to be prevented. More preferably, the milk proteins are casein or caseinate derived from cow's milk and the cross-linked casein or cross-linked caseinate are also derived from cow's milk.

Surprisingly, it has been found that casein or caseinates which have been cross-linked show a strongly reduced sensitization of the immune system of mammals, particularly humans. Hence, such cross-linked casein or caseinate proteins do not cause an allergy against milk proteins, such as cow's milk proteins. Hence, it is possible to prevent the development of an allergy against milk proteins such as casein or caseinate by administrating the cross-linked forms of these proteins.

On top of that, it has further been found that oral administration of the cross-linked casein or caseinate prior to sensitization with the native caseinate induces oral tolerance, meaning that the immune system is stimulated to develop a tolerogenic response against milk allergens, such as casein or caseinates. This is an advantage compared to extensively hydrolysed protein, which may be used to prevent sensitization, but will not induce oral tolerance, since in general these particles are too small to be recognized by the immune system. The current cross-linked casein or caseinate was able to induce oral tolerance while it also strongly reduced sensitization.

Without wishing to be bound by any theory it is believed that the cross-linking of casein or caseinate significantly reduces the allergenicity of these proteins to prevent sensitization and subsequent allergic reactions to these proteins. However, it is believed that the cross-linked casein or caseinate still contains some tolerizing epitopes which actively stimulate the immune system to develop a normal response against milk allergens.

In a preferred embodiment the cross-linked casein or cross-linked caseinate is used to prevent an allergy against casein, caseinate, milk serum protein, lactoferrin, transferrin or a combination thereof. These milk proteins are preferably derived from cow's milk.

Preferably, the cross-linked proteins according to the present invention are used to prevent an allergy, or induce oral tolerance, against casein, caseinate or a combination thereof.

In a preferred embodiment of the present invention the cross-linked protein has been cross-linked by means of an enzyme treatment, preferably by transglutaminase, more preferably a microbial transglutaminase. In a more preferred embodiment casein, caseinate or a combination thereof is cross-linked by means of a treatment with transglutaminase.

Transglutaminase is an enzyme that catalyses acyl-transfer reactions between γ-carboxyamide groups of glutamine residues and ε-amino group of lysine in proteins leading to inter-or intramolecular cross-linking. Commercially, transglutaminase is available from f.i. Ajinomoto Foods (Japan).

In view of the above, the cross-linked casein or cross-linked caseinate according to the present invention preferably comprises cross-links between γ-carboxyamide groups of glutamine residues and ε-amino group of lysine.

The use of transglutaminase in the cross-linking of casein by means of transglutaminase has already been described in WO01/70042, which is herewith incorporated by reference. However, in this document it has not been recognized that such cross-linked casein or caseinates can be used in the prevention of allergies against milk proteins, in particular for the prevention of allergies against casein or caseinates derived from cow's milk.

Preferably, the cross-linked protein, i.e. the cross-linked casein or cross-linked caseinate, has been prepared by exposing a composition, such as an aqueous solution, comprising 5-40 wt % of casein, caseinate or combination thereof to a cross-linking enzyme, preferably transglutaminase. Typically, 0.01-20 units cross-linking enzyme per gram of protein, preferably transglutaminase, are added to such a composition and allowed to react for 0.5 to 12 hours at 20-80° C. with the casein or caseinate in the composition.

The degree of cross-linking between the casein or caseinate molecules is preferably such that 0.1 to 2, preferably 0.5 to 1 cross-link per casein or caseinate molecule is formed.

After enzymatic cross-linking, the enzymes used, such as transglutaminase, are preferably inactivated. This can be done by heating the mixture of cross-linked casein or caseinate molecules with therein the enzymes to a given temperature for a certain amount of time. If transglutaminase is used, the enzymes are preferably inactivated by heating them for at least 3 minutes at 90° C. or higher.

In a preferred embodiment the cross-linked protein according to the present invention is administered to a human subject with an age up to 36 months, preferably 12 months, more preferably up to 6 months. During this period the immune system of humans is in development and has the highest risk of developing an allergy against milk proteins, such as cow's milk proteins. It is therefore highly preferred to only administer the cross-linked protein according to the present invention, e.g. casein or caseinate cross-linked by means of a cross-linking enzyme such as transglutaminase, instead of non-cross-linked casein or caseinate. This way, the sensitization of the human subject is avoided and the development of an allergy against milk proteins, such as casein or caseinate is prevented.

Furthermore, by administering the cross-linked casein or caseinate oral tolerance for milk proteins, such as casein or caseinate may be induced in such persons.

The above is even particularly relevant for human subjects which are predisposed to develop a milk protein allergy. For example human subjects which have relatives, such as a parent, brother or sister with an allergy for milk proteins, such as cow's milk proteins, and/or suffering from dermatitis and/or eczema.

A second aspect of the present invention relates to the use of the hypo-allergenic cross-linked casein or cross-linked caseinate as mentioned above for the prevention of an allergy against milk proteins, in particular against cow's milk proteins, more particularly against casein or caseinate derived from cow's milk. Preferably, the cross-linked casein or cross-linked caseinate is also derived from cow's milk.

A third aspect of the present invention relates to the use of the hypo-allergenic cross-linked casein or cross-linked caseinate as mentioned above for the induction of oral tolerance against milk proteins in mammals, preferably humans, most preferably infants, such as persons up to 12 months, preferably up to 6 months. Preferably, the cross-linked casein or cross-linked caseinate is derived from cow's milk.

A fourth aspect of the present invention relates to a method for the prevention of an allergy against milk proteins, such as casein and caseinate, and to a method for the induction of oral tolerance against such proteins, wherein the method comprises administering the cross-linked casein or cross-linked caseinate as mentioned above to a human subject, preferably a human subject up to 36 months, preferably 12 months, most preferably up to 6 months.

A fifth aspect of the present invention relates to a nutritional composition for use in the prevention of an allergy against milk proteins, such as casein or caseinate, or for use in the induction or oral tolerance against such proteins, wherein the nutritional composition comprises a hypo-allergenic cross-linked protein selected from cross-linked casein, cross-linked caseinate and combinations thereof.

The composition according to the present invention is preferably suitable for administration to human subjects with an age between up to 12 months, preferably up to 6 months. Hence, the nutritional composition is preferably formulated as a nutritional composition for infants.

The nutritional composition may comprise besides the cross-linked casein or caseinate other commonly used food components, preferably food components commonly used in infant food compositions, preferably food components used in hypo-allergenic infant food compositions.

Preferably, the nutritional composition comprises by weight of dry matter:

10 to 15% protein, of which at least 20%, preferably at least 30%, more preferably at least 40%, most preferably at least 50% is a cross-linked protein, said cross-linked protein being selected from cross-linked casein, cross linked caseinate and combinations thereof;

50 to 65% carbohydrates;
22 to 30% fat; and optionally
1-6% oligosaccharides.

In a preferred embodiment at least 80%, more preferably 90%, most preferably, all protein is cross-linked casein or cross-linked caseinate.

The carbohydrates preferably comprise by weight of dry matter 25-60% lactose, 5-15% starch, such as potato starch or corn starch.

In a preferred embodiment, the starch used comprises by weight of dry matter 5-20% hydrolysed starch, such as maltodextrins having a DE value (i.e dextrose-equivalent) of 15-20 or glucose syrup having a DE of 20-40.

Within the context of the present application the term fat includes both fats and oils. Preferably vegetable fats and oils are used, such as palm oil, canola oil, palm kernel oil, soy oil, sun flower oil, coconut oil, corn oil or combinations thereof. However, fish oil, single cell oil (e.g. algae derived), or milk fat oil or combinations thereof may also be used. Also polyunsaturated fatty acids (PUFA's) such as arachidonic acid (AA), docosahexaenoic acid (DHA) or eicosapentaenoic acid (EPA) may be used.

The oligosaccharides used are preferably galacto-oligosaccharides (GOS) having a degree of polymerization (DP) of between 2 to 8 and/or fructo-oligosaccharides having a DP of between 2 and 60. A sixth aspect of the present invention relates to a hypo-allergenic nutritional composition comprising a cross-linked protein being selected from cross-linked casein, cross-linked caseinate and combinations thereof.

Preferably, the hypo-allergenic nutritional composition comprises by weight of dry matter:
10 to 15% protein, of which at least 20%, preferably at least 30%, more preferably at least 40%, most preferably at least 50% is a cross-linked protein, said cross-linked protein being selected from cross-linked casein, cross linked caseinate and combinations thereof;
50 to 65% carbohydrates;
22 to 30% fat; and optionally
1-6% oligosaccharides.

In a preferred embodiment at least 80%, more preferably 90%, most preferably, all protein is cross-linked casein or cross-linked caseinate.

The carbohydrates preferably comprise by weight of dry matter 25-60% lactose, 5-15% starch, such as potato starch or corn starch.

In a preferred embodiment, the starch used comprises by weight of dry matter 5-20% hydrolyzed starch, such as maltodextrin having a DE value (i.e dextrose-equivalent) of 15-20 and/or glucose syrup having a DE of 20-40.

Within the context of the present application the term fat includes both fats and oils. Preferably vegetable fats and oils are used, such as palm oil, canola oil, palm kernel oil, soy oil, sun flower oil, coconut oil, corn oil or combinations thereof. However, fish oil, single cell oil (e.g. algae derived), or milk fat oil or combination thereof may also be used. Also polyunsaturated fatty acids (PUFA's) such as arachidonic acid (AA), docosahexaenoic acid (DHA) or eicosapentaenoic acid (EPA) may be used.

The oligosaccharides used are preferably galacto-oligosaccharides (GOS) having a degree of polymerization (DP) of between 2 to 8 and/or fructo-oligosaccharides having a DP of between 2 and 60.

The cross-linked protein has preferably been cross-linked by means of an enzymatic reaction, preferably by means of a treatment with transglutaminase.

In a preferred embodiment the cross-linked protein has been prepared by exposing a composition comprising 5-40 wt % of casein, caseinate or combination thereof to 0.01-20 units per gram protein of a cross-linking enzyme, such as transglutaminase, for 0.5 to 12 hours at 20-80° C.

The degree of cross-linking between the casein or caseinate molecules is preferably such that 0.1 to 2, preferably 0.5 to 1 cross-link per casein or caseinate molecule is formed. Furthermore, the cross-linked casein or cross-linked caseinate preferably comprises cross-links between γ-carboxyamide groups of glutamine residues and ε-amino group of lysine.

The composition according to the present invention is preferably suitable for administration to human subjects with an age up to 36 months, preferably 12 months, most preferably up to 6 months. Hence the nutritional composition is preferably formulated as a nutritional composition for infants.

In a preferred embodiment the nutritional composition is formulated as a powder, preferably such a powder is suitable for making a liquid composition after reconstitution with an aqueous solution, preferably with water. Most preferably, the composition according to the present invention is a powder to be reconstituted with water.

Preferably, the compositions according to the present invention are for providing the daily nutritional requirements to a human, in particular infants, including human subjects with an age up to 36 months, preferably 12 months, more preferably up to 6 months, most preferably humans at risk or predisposed for developing an allergy.

The invention will be explained further by the following non-limiting examples.

EXAMPLES

Example 1

Preparation of Cross-Linked Caseinate

A solution of sodium caseinate derived from cow's milk (20% wt % caseinate; viscosity 300 mPa·s at 70° C.) was reacted with the enzyme transglutaminase [E. C. 2.3.2.13] using 3 units of enzyme per gram caseinate for 1 hour at a temperature of 50° C.

The enzyme was deactivated by a heat treatment (90-120° C. for 30 to 2 minutes, respectively).

The cross-linked caseinate solution that has been treated to deactivate the enzyme activity was applied directly to the roller dryer (capacity 10-30 kg per hour) operating at a steam pressure of 2-3 bar and a roller speed of 10-20 rpm. The roller drier was a pilot machine of the make "GMF", equipped as a single drum drier. The drum had a diameter of 50 cm, and a length of 50 cm.

Despite its low protein concentration, an excellent protein film was formed on the drum. The dried film was removed by the built-in knives and fed to a milling machine and sieve. A white powder comprising cross-linked caseinate was obtained.

Example 2

In Vivo Sensitization Experiments with Cross-Linked Caseinate and Caseinate

In these experiments cross-linked caseinate and native caseinate were tested in both the sensitization and challenge effector phase of the allergic immune response to assess the sensitizing capacity and the allergenicity of cross-linked caseinate and native caseinate.

2.1 Material & method

The cross-linked caseinate of example 1 was used in these experiments. As native caseinate EM7 from Friesland-Campina DMV was used. The in vivo experiments were carried out on the following treatment groups:

TABLE 1 set up of treatment groups

| | Sensitization | Challenge |
|---|---|---|
| Non-sensitized control/challenge caseinate | CT* | caseinate |
| Sensitization caseinate/challenge caseinate | CT + caseinate | caseinate |
| Sensitization cross-linked caseinate/challenge caseinate | CT + cross-linked caseinate | caseinate |

*CT: Cholera Toxin, commonly used adjuvant to induce an allergy in this mouse model 2.2 Oral Sensitization of Mice with Cross-Linked Caseinate and Native Caseinate Three-week-old specific pathogen-free female C3H/HeOuJ mice were purchased from Charles River Laboratories (Saint Germain sur l'Arbresle, France), and maintained on semi-purified cow's milk protein-free mouse chow (Research Diet Services, Wijk bij Duurstede, The Netherlands). Animal care and use were performed in accordance with the guidelines of the Dutch Committee of Animal Experiments. To investigate the sensitizing capacity of cross-linked caseinate in comparison to native caseinate, mice were orally sensitized with a blunt needle on day 0, 7, 14, 21 and 28 with 20 mg cross-linked caseinate or caseinate homogenized in PBS (0.5 ml, Cambrex Bio Science, Verviers, Belgium) mixed with 10 µg cholera toxin (Quadratech Diagnostics, Epsom, UK) as an adjuvant. Non-sensitized mice received cholera toxin in PBS only. One week after the last oral sensitization anaphylactic reactions and body temperature changes were determined after an intradermal native caseinate challenge. After 24 hours, mice were challenged orally with 50 mg native caseinate or cross-linked caseinate and 30 minutes later blood samples were collected. Blood samples were centrifuged for 15 minutes at 13,500 rpm and sera were stored at −20° C.

2.3 Anaphylactic Shock Score and Body Temperature

To evaluate the residual sensitization capacity of cross-linked caseinate and native caseinate, the anaphylactic reactions and body temperature were determined as clinical related symptoms after intradermal cross-linked caseinate or native caseinate challenge. To establish the severity of the shock, a validated anaphylactic scoring table was used (table 2), as adapted from Li et al. (Li et al., 1999). To measure changes in body temperature, all mice received an implantable electronic ID transponder (Bio Medic Data Systems, Delaware, USA) in order to measure the individual body temperature.

TABLE 2

Anaphylactic symptoms scoring table

| Score | Symptoms |
|---|---|
| 0 | No symptoms |
| 2 | Scratching nose and mouth |
| 3 | Swelling around the eyes and mouth; piloerection; reduced activity; higher breathing rate |
| 4 | No activity after stimulation, shivering and muscle contractions |
| 5 | Death by shock |

2.4 Measurement of mMCP-1 and Caseinate-Specific Serum IgE

Concentrations of allergen-specific IgE were determined in serum by means of ELISA as described previously (van Esch et al., Clinical Experimental Allergy; 2009). In short, Microlon plates (Greiner Bio-one, Monroe, USA) were coated with allergen for 18 hours at 4° C. Plates were washed after each incubation step. Serum samples were applied and incubated for 2 hours at room temperature (RT), followed by incubation with biotin-labeled rat anti-mouse IgE for 90 minutes at RT. The plates were incubated with streptavidin-horseradish peroxidase for 1 hour at RT and developed with o-phenylendiamine (Sigma-Aldrich). The reaction was stopped with 4 M $H_2SO_4$ and absorbance was measured at 490 nm on a Benchmark microplate reader (Bio-Rad, Hercules, Calif., USA). Serum concentrations of mouse mast cell protease-1 (mMCP-1) were determined according to the manufacturer's protocol using a commercially available ELISA kit (Moredun Scientific Ltd., Midlothian, UK).

2.5 Statistical Analysis

Statistical analysis of the mast cell mediator mMCP-1 in serum was performed using a 1-way ANOVA and post hoc Bonferroni's multiple comparison test. The anaphylactic shock scores, specific-IgE and bodytemperature were statistically analyzed using the Kruskal-Wallis test followed by the Dunn's multiple comparison test because variances differed significantly. All statistical analyses were conducted using GraphPad Prism software (version 4.03).

Results 2.6 Anaphylactic Shock Score

Sensitizing Capacity

After intradermal caseinate challenge, the non-sensitized mice did not show any anaphylactic shock symptoms and the caseinate sensitized mice responded with serious anaphylactic shock symptoms (score=3). In contrast to sensitization with native caseinate sensitized mice, no anaphylactic shock symptoms were observed in mice sensitized to cross-linked caseinate according to the present invention.

2.7 Body Temperature

Sensitizing Capacity

Body temperatures were measured 30 minutes after intradermal caseinate challenge in sensitized mice. The results of the measurements are depicted in Table 3.

TABLE 3

Body temperature after intradermal caseinate

| Sensitization | Average body temperature | SEM (p < 0.01) |
|---|---|---|
| Non-sensitized | 37.2 | 0.061 |
| Caseinate | 32.9 | 0.90 |
| Cross-linked caseinate | 38.2 | 0.11 |

A significant drop in body temperature was observed 30 minutes after intradermal challenge in mice sensitized to caseinate compared to non-sensitized mice. No drop in body temperature was observed in mice sensitized to cross-linked caseinate. (Anova followed by student t-test; p=0.022).

These results indicate that based on body temperature the sensitizing capacity of cross-linked caseinate is dramatically reduced compared to the native caseinate.

2.8 mMCP-1 Serum Concentrations
Sensitizing Capacity

Serum mMCP-1 levels were measured 30 minutes after oral challenge. The results are shown in Table 4.

TABLE 4 mMCP-1 levels after oral caseinate challenge

| Sensitization | mMCP-1 (ng/ml) | SEM (p < 0.001) |
|---|---|---|
| Non-sensitized | 158.6 | 43.04 |
| Caseinate | 1637.0 | 84.60 |
| Cross-linked caseinate | 292.2 | 67.22 |

Elevated levels of mMCP-1 were measured in native caseinate sensitized mice compared to non-sensitized mice. Oral challenge in mice sensitized to cross-linked caseinate did not result in significantly increased mMCP-1 levels compared to non-sensitized mice.

To investigate whether a reduced sensitization to cross-linked caseinate was observed, mMCP-1 serum concentrations in cross-linked caseinate sensitized mice were compared to the elevated mMCP-1 concentrations in native caseinate sensitized mice. Indeed, mMCP-1 concentrations in cross-linked caseinate sensitized mice were reduced to the level of non-sensitized mice. These results indicate that sensitization with cross-linked caseinate did not induce intestinal mast cell degranulation.

2.9 Caseinate-Specific IgE

In contrast to cross-linked caseinate sensitized mice, elevated levels of caseinate-specific IgE were measured in mice sensitized to the native caseinate. The results are depicted in Table 5.

TABLE 5

Levels of caseinate specific IgE

| Sensitization | Caseinate-IgE (OD) | SEM (p < 0.05) |
|---|---|---|
| Non-sensitized | 0.060 | 0.025 |
| Caseinate | 0.916 | 0.200 |
| Cross-linked caseinate | 0.454 | 0.136 |

There was a reduction in specific serum IgE in mice sensitized to cross-linked caseinate compared to native caseinate-sensitized mice. Based on specific-IgE levels in combination with the decreased risk for developing clinical related symptoms, data point to a decreased risk for cow's milk allergy if mice are sensitized with cross-linked caseinate compared to caseinate.

Example 3

In Vivo Tolerance Experiments with Cross-Linked Caseinate and Caseinate

In these experiments the capacity of cross-linked caseinate according the present invention to induce oral tolerance to the native caseinate was tested in a mouse model for cow's milk allergy. C3H/HeOuJ female mice of 4 weeks old were used.

3.1 Material & Method

For the tolerance experiments the method was used as described in example 2, preceded with a pretreatment with PBS, caseinate, cross-linked caseinate or extensively hydrolyzed caseinate CE90STL (FrieslandCampina DOMO, USA) (in absence of cholera toxin) by administering oral gavages daily, from day −7 until day −2 (50 mg per day per mouse). For the sensitization oral gavages with caseinate were administered to the mice on day 0, 7, 14, 21 and 28 using cholera toxin as adjuvant. On day 33, intradermal challenge with caseinate or casein was carried out. One hour after the challenge the acute anaphylactic shock score and body temperature were measured. On Day 35 oral challenge with caseinate or casein was carried out for measurement of the mucosal mast cell mediator mMCP-1.

TABLE 5 set up of treatment groups

| Group | Pre-treatment | Sensitization | Challenge |
|---|---|---|---|
| Group 1 | PBS | No Sensitization | caseinate |
| Group 2 | PBS | Sensitization with caseinate | caseinate |
| Group 3 | Caseinate | Sensitization with caseinate | caseinate |
| Group 4 | Cross-linked caseinate | Sensitization with caseinate | caseinate |
| Group 5 | Extensively hydrolyzed caseinate | Sensitization with caseinate | caseinate |

Results 3.2 Anaphylactic Shock Score, Tolerance Induction

In PBS pre-treated animals, the non-sensitized animals (group 1) did not show any anaphylactic shock symptoms (anaphylactic score=0). The PBS pre-treated mice, sensitized with caseinate (group 2) responded with moderate anaphylactic shock symptoms (score=2). Also the animals pre-treated with extensively hydrolyzed caseinate and sensitized with caseinate (group 5) responded with serious anaphylactic shock symptoms, indicating that no tolerance was developed for the intact protein (score=2). As expected, pretreatment of naïve mice with caseinate (group 3) decreased sensitization towards caseinate, suggesting induction of oral tolerance (score=0). In contrast to pretreatment with extensively hydrolyzed caseinate (group 5), pre-treatment with cross-linked caseinate according to the present invention (group 4) prevented the animals from sensitization towards caseinate (score=0), indicating that cross-linked caseinate induced oral tolerance for caseinate.

3.3 Body Temperature

A significant drop in body temperature was observed 30 minutes after intradermal challenge in the PBS pre-treated mice sensitized to caseinate (group 2) compared to the non-sensitized mice (group 1). This drop was also observed in animals pre-treated with extensively hydrolysed caseinate and sensitized with caseinate (group 5), indicating that no tolerance was developed for the intact protein. As expected, no drop in body temperature was observed in animals pre-treated with caseinate and sensitized with caseinate (group 3), suggesting induction of oral tolerance. In contrast to treatment with extensively hydrolyzed caseinate, no drop in body temperature was observed in mice pretreated with cross-linked caseinate according to the present invention and sensitized to caseinate (group 4), indicating that cross-linked caseinate induced oral tolerance for caseinate.

TABLE 6

Body temperature after intradermal challenge

|  | Average body temperature | SEM (p < 0.01) |
|---|---|---|
| Group 1 | 38.6 | 0.14 |
| Group 2 | 33.1 | 1.2 |
| Group 3 | 36.2 | 1.4 |
| Group 4 | 37.6 | 0.60 |
| Group 5 | 34.9 | 1.5 |

3.4 mMCP-1 Serum Concentrations

Serum mMCP-1 levels were as follows in the different groups.

TABLE 7 mMCP-1 levels after oral challenge

|  | mMCP-1 (ng/ml) | SEM (p < 0.01) |
|---|---|---|
| Group 1 | 16951 | 1888 |
| Group 2 | 84202 | 20081 |
| Group 3 | 40037 | 3925 |
| Group 4 | 50419 | 27940 |
| Group 5 | 140081 | 14579 |

Both the group of PBS pre-treated mice sensitized with caseinate (group 2) and the group of mice pre-treated with extensively hydrolyzed caseinate (group 5) showed a clear increase of mMCP-1 levels. This indicates that no oral tolerance has developed for caseinate. In the group of mice pre-treated with caseinate and sensitized with caseinate (group 3) no serious increase of mMCP-1 levels was observed. Also in the group of mice pre-treated with the cross-linked caseinate and sensitized with caseinate (group 4) no serious increase of mMCP-1 levels was observed, indicating that cross-linked caseinate according to the present invention induced oral tolerance to caseinate.

3.5 Caseinate-Specific IgE

In contrast to cross-linked caseinate pre-treated mice (group 4) and mice pre-treated with caseinate and sensitized with caseinate (group 3), the mice pre-treated with the extensively hydrolyzed caseinate (group 5) showed an increased level of caseinate specific IgE. Also the PBS pre-treated and with caseinate sensitized mice (group 2) showed an increased level of caseinate specific IgE.

TABLE 8

Levels of caseinate specific IgE

|  | Caseinate-IgE (OD) | SEM (P < 0.05) |
|---|---|---|
| Group 1 | 0 | 0 |
| Group 2 | 1064 | 147.5 |
| Group 3 | 156.1 | 83.1 |
| Group 4 | 53.0 | 21.1 |
| Group 5 | 1061 | 357.3 |

The invention claimed is:

1. A method of reducing the risk of developing an allergy against milk proteins in a human subject predisposed to develop a milk protein allergy by inducing oral tolerance against milk proteins, comprising orally administering to the human subject a composition comprising, by weight of dry matter:
   (a) 10 to 15% protein, of which at least 20% is a hypo-allergenic cross-linked protein selected from cross-linked casein, cross-linked caseinate and combinations thereof;
   (b) 50 to 65% carbohydrates;
   (c) 22 to 30% fat and optionally
   (d) 1-6% oligosaccharides.

2. The method according to claim 1, wherein the milk protein is casein, caseinate, milk serum protein, lactoferrin, transferrin or a combination thereof.

3. The method according to claim 2, wherein the milk protein is casein, caseinate or both.

4. The method according to claim 1, wherein the cross-linked protein has been cross-linked by enzymatic treatment.

5. The method according to claim 1, wherein the cross-linked protein comprises on average 0.1 to 2 cross-links per casein or caseinate molecule.

6. The method according to claim 5, wherein the cross-linked protein comprises on average 0.5 to 1 cross-links per casein or caseinate molecule.

7. The method according to claim 1, wherein the human subject is up to 36 months of age.

8. The method according to claim 4, wherein the enzymatic treatment is with transglutaminase.

9. A method of reducing the risk of developing an allergy against milk proteins in a human subject up to 36 months of age by inducing oral tolerance against milk proteins, comprising orally administering to the human subject a composition comprising, by weight of dry matter:
   (a) 10 to 15% protein, of which at least 20% is a hypo-allergenic cross-linked protein selected from cross-linked casein, cross-linked caseinate and combinations thereof;
   (b) 50 to 65% carbohydrates;
   (c) 22 to 30% fat and optionally
   (d) 1-6% oligosaccharides.

10. The method according to claim 9, wherein the milk protein is casein, caseinate, milk serum protein, lactoferrin, transferrin or a combination thereof.

11. The method according to claim 10, wherein the milk protein is casein, caseinate or both.

12. The method according to claim 9, wherein the cross-linked protein comprises on average 0.1 to 2 cross-links per casein or caseinate molecule.

13. The method according to claim 12, wherein the cross-linked protein comprises on average 0.5 to 1 cross-links per casein or caseinate molecule.

14. The method according to claim 9, wherein the human subject is predisposed to develop a milk protein allergy.

15. A method of reducing the risk of developing an allergy against milk proteins in a human subject in need thereof by inducing oral tolerance against milk proteins, comprising orally administering to the human subject a composition comprising, by weight of dry matter:
   (a) 10 to 15% protein, of which at least 20% is a hypo-allergenic cross-linked protein selected from cross-linked casein, cross-linked caseinate and combinations thereof;
   (b) 50 to 65% carbohydrates;
   (c) 22 to 30% fat and optionally
   (d) 1-6% oligosaccharides,
   wherein the cross-linked protein comprises on average 0.1 to 2 cross-links per casein or caseinate molecule.

16. The method according to claim 15, wherein the milk protein is casein, caseinate, milk serum protein, lactoferrin, transferrin or a combination thereof.

17. The method according to claim 16, wherein the milk protein is casein, caseinate or both.

18. The method according to claim 17, wherein the cross-linked protein comprises on average 0.5 to 1 cross-links per casein or caseinate molecule.

19. The method according to claim 15, wherein the human subject is up to 36 months of age.

20. The method according to claim 15, wherein the human subject is predisposed to develop a milk protein allergy.

* * * * *